(12) United States Patent  
Britt et al.

(10) Patent No.: US 9,205,254 B1  
(45) Date of Patent: Dec. 8, 2015

(54) FACIAL MUSCLE TONER SYSTEM

(71) Applicant: Shannon Gilbreth Britt, Franklin, TN (US)

(72) Inventors: Shannon Gilbreth Britt, Franklin, TN (US); Klaus Rosburg, Brooklyn, NY (US)

( * ) Notice: Subject to any disclaimer, the term of this patent is extended or adjusted under 35 U.S.C. 154(b) by 173 days.

(21) Appl. No.: 13/904,632

(22) Filed: May 29, 2013

Related U.S. Application Data

(63) Continuation-in-part of application No. 13/900,252, filed on May 22, 2013, and a continuation of application No. 13/098,114, filed on Apr. 29, 2011.

(60) Provisional application No. 61/329,449, filed on Apr. 29, 2010.

(51) Int. Cl.  
*A61H 1/00* (2006.01)  
*A61N 1/32* (2006.01)

(52) U.S. Cl.  
CPC ..................... *A61N 1/322* (2013.01)

(58) Field of Classification Search  
CPC .............................. A61N 7/00; A61H 23/0245  
See application file for complete search history.

(56) References Cited

U.S. PATENT DOCUMENTS

| | | | |
|---|---|---|---|
| 6,308,104 B1 * | 10/2001 | Taylor et al. | 607/118 |
| 7,018,345 B2 | 3/2006 | Mori et al. | |
| 8,639,361 B2 | 1/2014 | Nathanson | |
| 2007/0232966 A1 * | 10/2007 | Applebaum et al. | 601/17 |

* cited by examiner

*Primary Examiner* — Tse Chen  
*Assistant Examiner* — Hien Nguyen  
(74) *Attorney, Agent, or Firm* — Shane V. Cortesi

(57) ABSTRACT

A facial muscle toner system is provided that includes, in some embodiments, a base unit and a hand piece unit. The base unit optionally includes a display portion at a front face and a command portion including one or more keys. The hand piece unit is operably connected to the base unit and is located remotely from the base unit. The hand piece unit includes a housing having a receptacle portion and a therapy distribution instrument extending from the receptacle portion. The therapy distribution instrument is configured to distribute therapy to sub-dermal facial muscles.

17 Claims, 14 Drawing Sheets

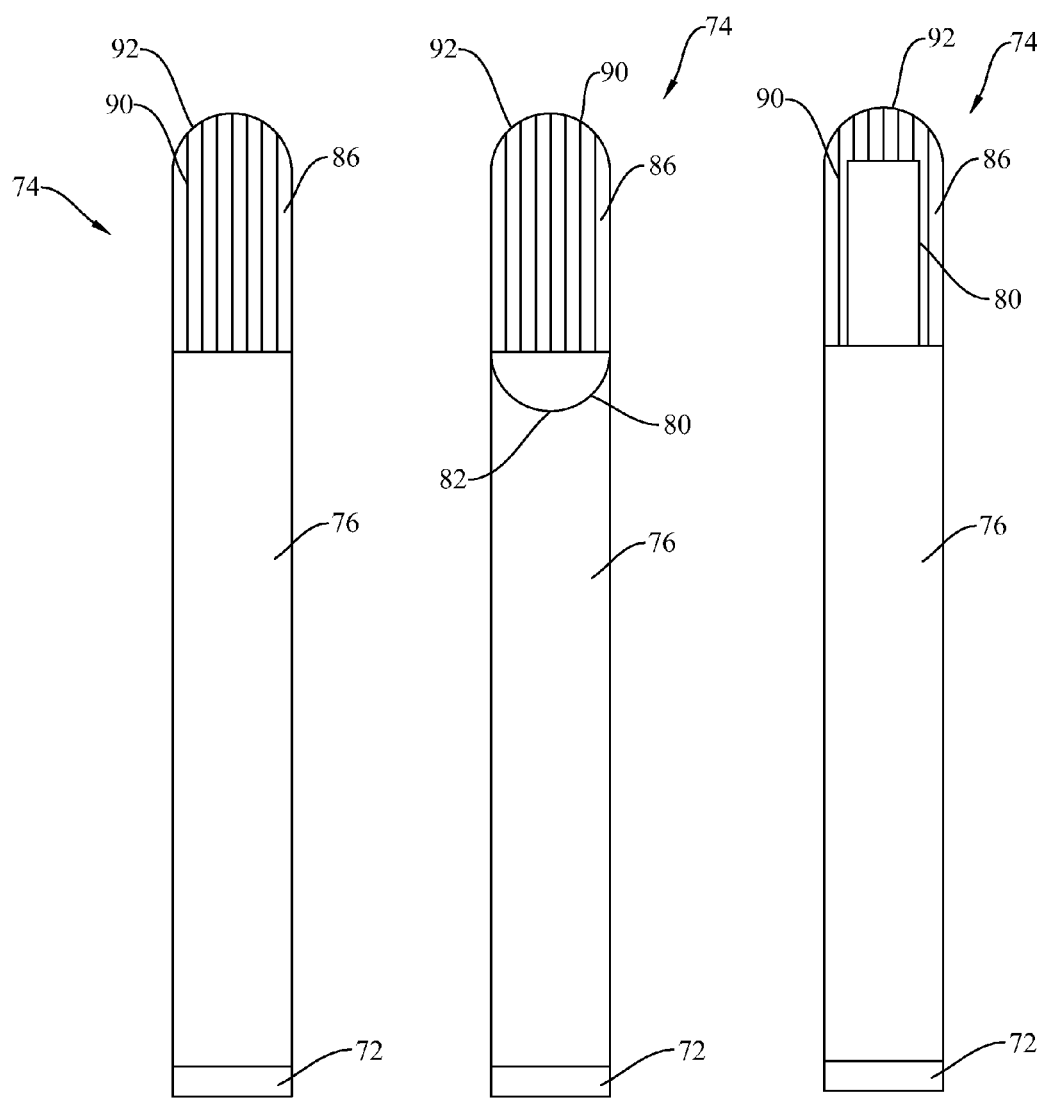

FACIAL MUSCLE TONER SYSTEM

CROSS REFERENCE TO RELATED APPLICATIONS

This application is a continuation-in-part of U.S. patent application Ser. No. 13/900,252, filed May 22, 2013, which is a continuation of U.S. patent application Ser. No. 13/098,114, filed Apr. 29, 2011, which claims the benefit of U.S. Provisional Application No. 61/329,449, filed Apr. 29, 2010. The contents of U.S. patent application Ser. No. 13/900,252, U.S. patent application Ser. No. 13/098,114 and U.S. Provisional Application No. 61/329,449 are incorporated herein by reference in their entirety as if fully set forth herein.

BACKGROUND OF THE INVENTION

1. Field of the Invention

The present invention generally relates to a facial muscle toner system. More specifically, the present invention relates to a facial muscle toner system that is portable and has interchangeable therapy distribution instruments.

2. Background Information

Electrical micro-current stimulation has proven to be an effective method of improving facial skin tone. The method is effective enough that a flourishing industry provides medical treatments and devices which apply micro-current to sub-dermal muscles of a human face to improve facial skin appearance. In general, such devices work by causing a contraction of the facial muscles to re-educate the muscles.

There are around a dozen groups of facial muscles, with a total number of facial muscles, depending on the method of counting, that may range as high as roughly one hundred. These muscles are crucial to human identity and self-expression, as the face is the primary nonverbal communication device used by human beings.

Previous attempts at stimulation to improve facial skin tone have included an apparatus with a large cumbersome control body that houses control components. The large control body is connected to two electrodes applied to a face. The control body and electrodes are not easy for transporting to other locations. Furthermore, the electrodes are permanently attached to the control body and do not offer the operator multiple options for stimulation therapy.

In view of the above, it will be apparent to those skilled in the art from this disclosure that there exists a need for an improved facial muscle toner system that is portable and has interchangeable therapy distribution instruments. This invention addresses this need in the art as well as other needs, which will become apparent to those skilled in the art from this disclosure.

SUMMARY OF THE INVENTION

A facial muscle toner system is provided that, in some embodiments, basically comprises a base unit and a hand piece unit. The base unit optionally includes a display portion at a front face and a command portion including one or more keys. The hand piece unit is operably connected to the base unit and is located remotely from the base unit. The hand piece unit includes a housing having a receptacle portion or stem and a therapy distribution instrument extending from the receptacle portion or stem. The therapy distribution instrument includes a therapy portion to distribute therapy to sub-dermal facial muscles.

Another embodiment of a facial muscle toner system is provided that, in some embodiments, basically comprises a hand piece unit and a base unit. The hand piece unit includes a housing having a receptacle portion or stem and a therapy distribution instrument. The therapy distribution instrument includes a first rigid member, a second rigid member, optionally a first actuator and optionally a second actuator. In some embodiments, the first rigid member has a substantially straight lower portion and a curvature at an upper portion that curves across the width of the receptacle portion. The first rigid member has a first contact section disposed at an end portion of the first rigid member. The second rigid member extends upwardly away from the receptacle portion or stem and includes a second contact section disposed at an end portion of the second rigid member. The optional first actuator is connected to an end portion of the first rigid member and slidably disposed on an exterior surface of the hand piece unit. The optional second actuator is connected to an end portion of the second rigid member and slidably disposed on an exterior surface of the hand piece unit opposite the first actuator. The base unit has electronic components to control the hand piece unit. The electronic components are optionally disposed in the hand piece unit and one or more of the electronic components are electrically connected to the first and second contact sections to deliver a micro-current. In other embodiments, as opposed to first and second actuators, the system includes a pivot pin that is configured to allow the second rigid member to move relative to the first rigid member. In both embodiments (i.e., those with actuators and those with a pivot pin), the distance between the first and second contact sections can be varied by a user moving the first and/or second rigid members. In some embodiments, the micro-current is between 100-900 microamps.

BRIEF DESCRIPTION OF THE DRAWINGS

Referring now to the attached drawings which form a part of this original disclosure:

FIG. 12 is a side view of another embodiment of the therapy tip portion having a plastic tip;

FIG. 13 is a side view of another embodiment of the therapy tip portion with a plastic tip and LED;

FIG. 14 is a side view of another embodiment of the therapy tip portion with a plastic tip and LED;

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
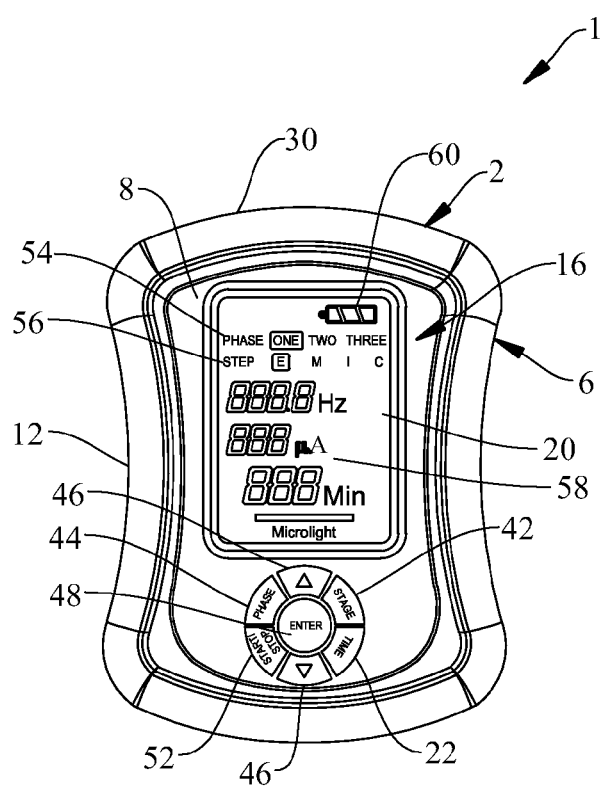
FIG. 1 is a front plan view of a base unit of a facial muscle toner system in accordance with an embodiment of the present invention.

Referring initially to FIG. 1, a facial muscle toner system 1 is illustrated in accordance with a first embodiment of the present invention. The facial muscle toner system 1 provides convenience to an operator and offers multiple options for stimulation of facial muscles, shortening and/or elongating facial muscles or a combination thereof. The present invention is advantageously designed for self-use and therefore, operator as used herein can refer to the patient or a care giver.

The facial muscle toner system 1 may include a base unit 2 and one or more hand piece units 4 attached to the base unit 2. The base unit 2 is sized and configured for optimal convenience. That is, an operator can connect the base unit 2 to apparel such as, for example, a belt or smock. The base unit 2 offers lightweight and portable protection of components therein by comprising a resilient housing 6 comprised of a lightweight plastic to form a rigid housing about the components. Preferably, the housing 6 has contours for ergonomic fit with an operator's hand. The housing 6 includes a front face 8, a back face 10, and side portions 12, 14.

Referring to FIGS. 1-3B, embodiments of the base unit 2 will now be discussed. It will be apparent to those skilled in the art from this disclosure that the following descriptions of the base unit 2 are provided for illustration only and not for the purpose of limiting the invention. The base unit 2 further includes a display portion 16 at the front face 8 and a connection mechanism 18 at the back face 10. The display portion 16 includes a display 20 and a command portion 22. The display portion 16 provides information to the operator via the display 20 and also provides an interface for the operator to implement various functions, modes or programming of the system 1 via the command portion 22. The connection mechanism 18 is connected to the back face 10 and is configured and arranged to attach to an operator's apparel or nearby convenient structure, such as a bed, for example. The base unit 2 can be of a tabletop design that allows the user to rest the base unit 2 on a surface without having to carry the base unit 2. The connection mechanism 18 can also be replaced with a stand hingedly connected to the base unit 2 and having outwardly extending legs so that the base unit 2 can stand on a surface.

Figure 2:
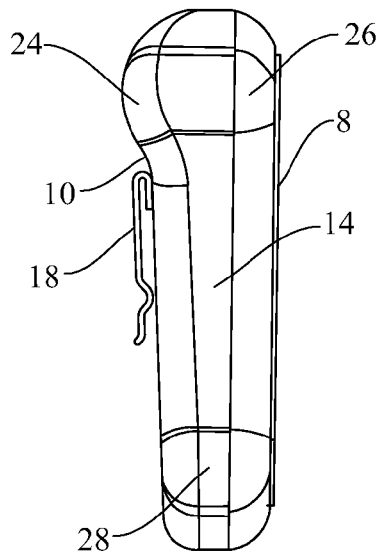
FIG. 2 is a side plan view of the base unit of FIG. 1.

In the embodiment shown in FIGS. 1 and 2, the connection mechanism 18 includes a belt clip but could easily include other structures such as a strap with a snap, for example. The back face 10 forms a leg portion 24 at a top portion 26 of the housing 8 to tilt the base unit 2 at an angle for better viewing. Specifically, the leg portion 24 extends further from the front face 8 than a bottom portion 28 of the housing 6 so as to slightly lift the top portion 26 upwardly when the base unit 2 is at rest on a substantially horizontal surface.

The base unit 2 further includes an auxiliary information unit 30 electrically connected to electronic components 32 disposed in the housing 8. The auxiliary information unit 30 provides a connection or access to additional data or information for the convenience of the operator. For example, the auxiliary information unit 30 can include one or more of an I/O port, USB, a cartridge holder or wireless communication unit, for example. With the auxiliary information unit 30, the operator can send or receive data or can record or transmit data to an external storage medium. The operator can also receive software updates or information for additional functionality, for example.

Figure 3A:
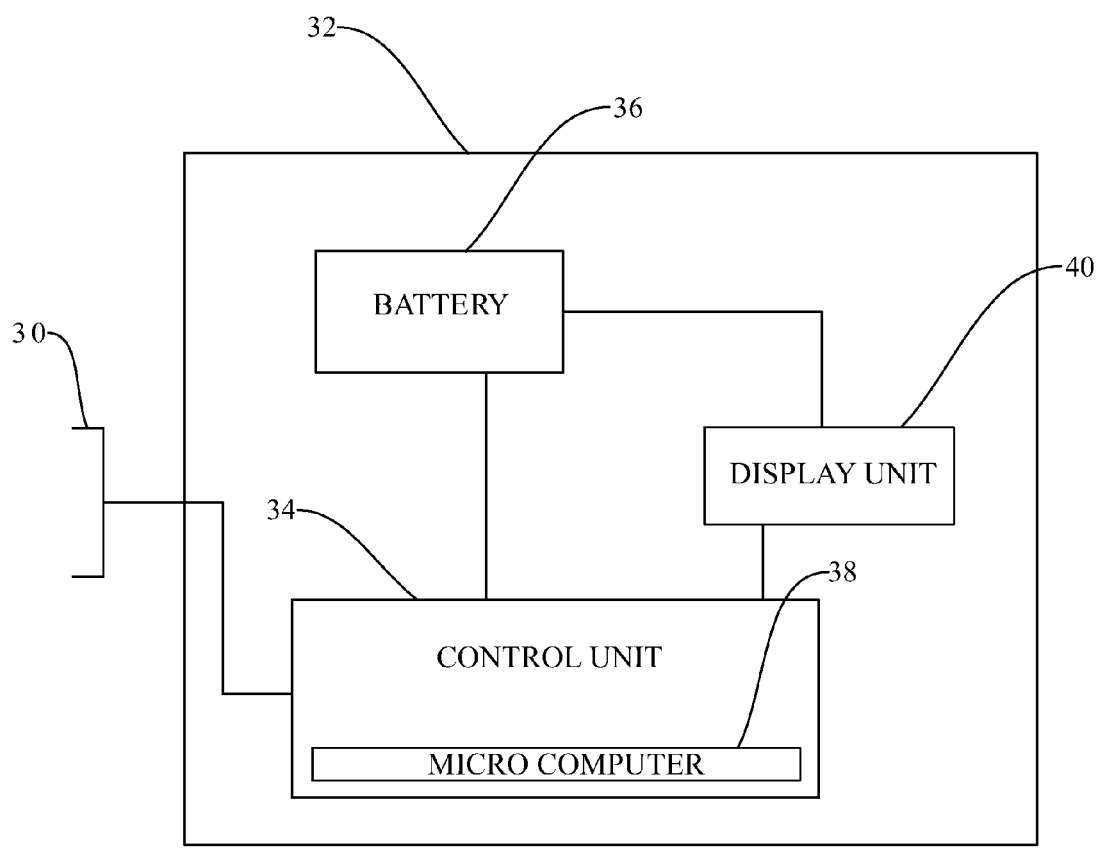
FIG. 3A is a schematic view of one embodiment of electronic components in the base unit and an auxiliary information unit.
Figure 3B:
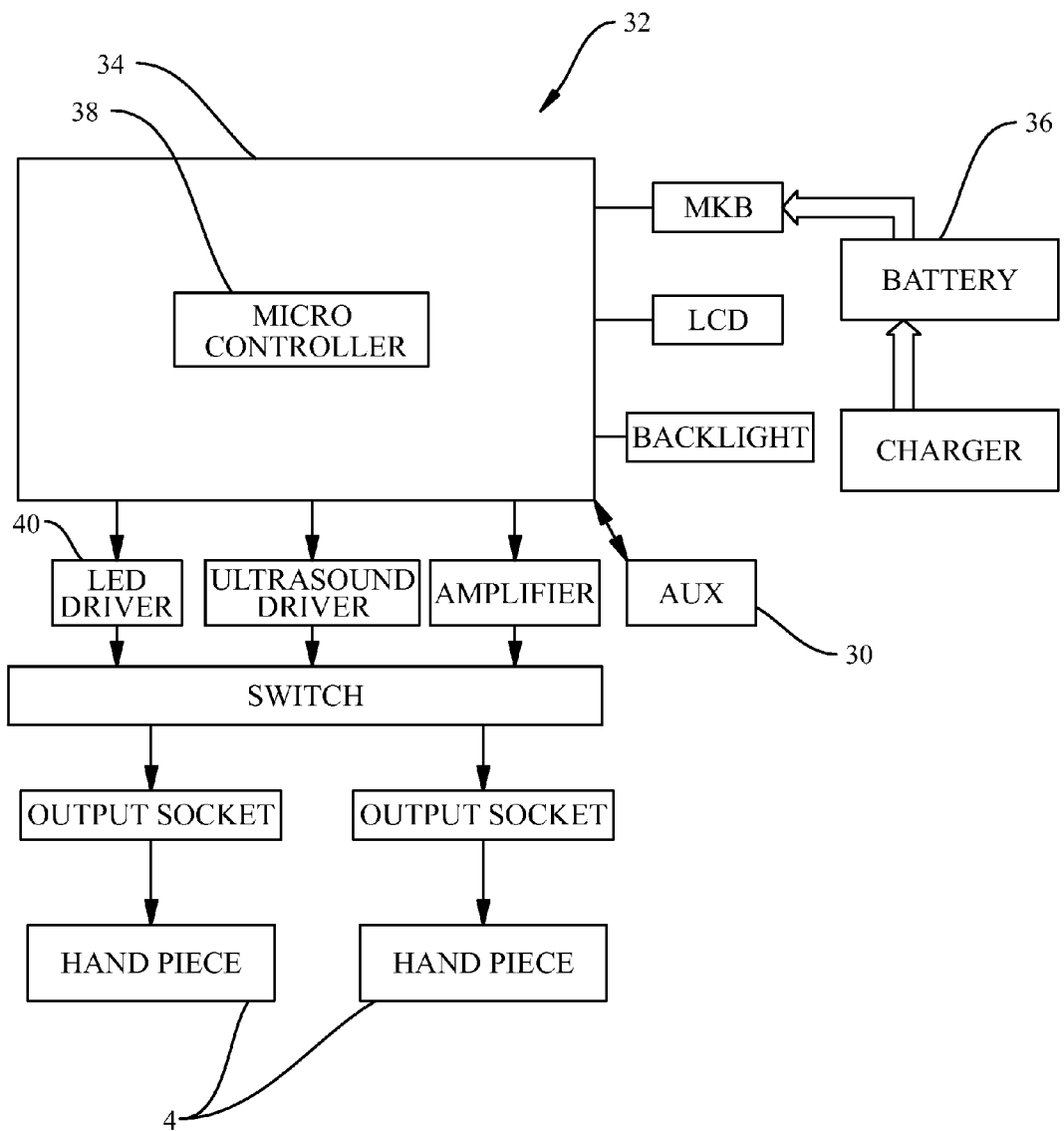
FIG. 3B is a schematic view of another embodiment of electronic components in the base unit and an auxiliary information unit.

The interior of the housing 6 is sized and configured to receive the electronic components 32 housed in the base unit 2. Referring to FIGS. 3A and 3B, the electronic components 32 include a control unit 34 and a rechargeable battery 36. The control unit 34 preferably includes a microcomputer 38 with a control program that controls the facial muscle toning system 1. The control unit 34 can also include other conventional components such as an input interface circuit, an output interface circuit, and a memory circuit having storage devices such as a ROM (Read Only Memory) device and a RAM (Random Access Memory) device. The microcomputer 38 of the control unit 34 is programmed to control the functions selected at the base unit 2. It will be apparent to those skilled in the art from this disclosure that the precise structure and algorithms for the control unit 34 can be any combination of hardware and software that will carry out the functions of the present invention. In other words, any function as described in the specification and claims should include any structure or hardware and/or algorithm or software that can be utilized to carry out the described function.

The rechargeable battery 36 powers the control unit 34 and is connected to a recharging apparatus such as a USB, inductance charger, an AC/DC charge port, a docking station or a combination thereof. The electronic components 34 further include a display unit 40 for generating data to display at the display 20 of the display portion 16. The rechargeable battery 36 powers the display 20 and the display unit 40.

Referring to FIG. 1, the command portion 22 includes a plurality of input instruments 42 for conveying the selection of an operator. In the embodiment shown in FIGS. 1 and 2, the input instruments 42 are input indicators or keys disposed adjacent the display portion 16 at a bottom portion of the front face 8. However, the command portion 22 can be disposed adjacent the display portion 16 on the side portion(s) 12, 14 of the base unit 2. The keys include two or more mode keys 44, two or more direction keys 46, one or more selector keys 48, one or more power key 50, and one or more operation (start/stop) key 52. It will be apparent to one of ordinary skill in the art from this disclosure that the input instruments 42 can be various pressure or heat sensitive input indicators that convey the operator's selection to the control unit 34. Furthermore, the number of input indicators can be greater or less than that shown, as needed to facilitate operator input.

The input instruments 42 can be used to navigate a menu displayed on the display 20 to select different light or micro-current therapies or different combinations of therapies. Although the base unit 2 and the hand piece unit 4 may be configured such that the base unit 2 senses the configured hand piece unit 4 and automatically engages a corresponding mode of operation, the phase or modes of operation for each hand piece unit 4 can also be selected using the input instruments 42. Referring now to FIG. 1, the display 20 includes a phase section 54, a mode section 56, a quantitative section 58 and a battery life section 60. The phase section 54 displays the phases that are available for selection as well as the currently selected phase. The mode section 56 displays the designated steps required for the certain mode of therapy and displays the current step. The quantitative section 58 displays the light frequency, the microcurrent in real time and/or a timer for displaying the length of time that the therapy has been applied. The battery life section 60 displays a graphical or pictorial representation of a battery to indicate the remaining charge in the rechargeable battery 36.

The hand piece unit 4 is operably connected to the base unit 2 via cables 62 that conduct electrical power to the hand piece units 4. The cable 62 may also deliver command signals to the respective hand piece unit 4. Each of the hand piece units 4 is located separately from the base unit 2 and is freely movable for optimal positioning on an operator's face without sizeable restrictions. The hand piece unit 4 is utilized in conjunction with the base unit 2 and another hand piece unit 4 to shorten or elongate facial muscles using stretching, or re-educate facial muscles using micro-current and/or light therapy.

Figure 4:
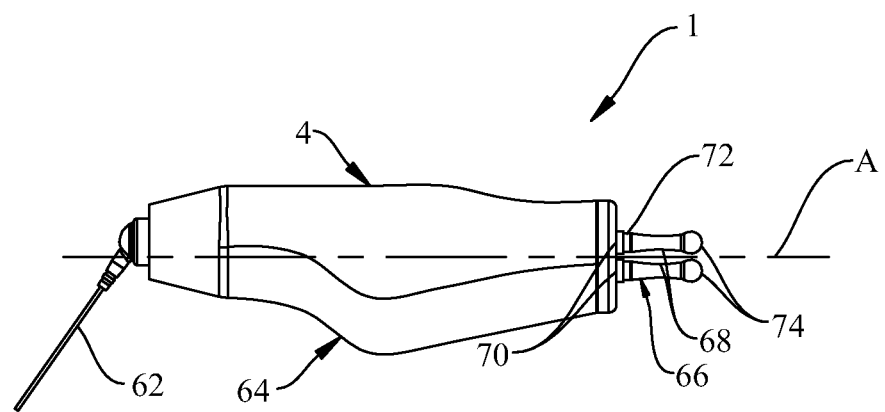
FIG. 4 is a side plan view of an embodiment of a hand piece unit of the facial muscle toner system wherein probes are connected externally.
Figure 5:
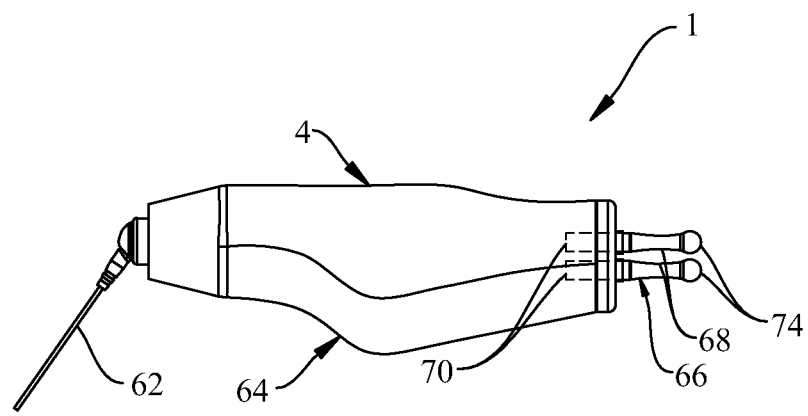
FIG. 5 is a side plan view of an embodiment of a hand piece unit of the facial muscle toner system wherein probes are connected internally.
Figure 6:
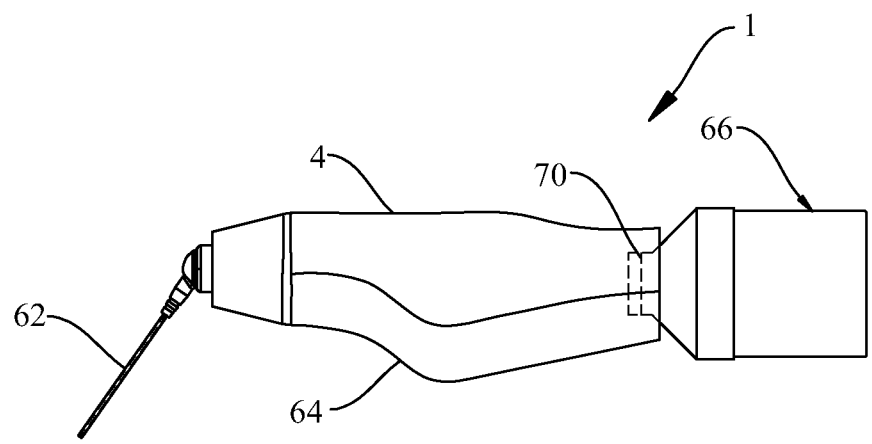
FIG. 6 is a side plan view of an embodiment of a hand piece unit of the facial muscle toner system wherein a thin metal blade for ultrasonic exfoliation is connected to the hand piece unit.

Referring to FIGS. 4-6, the hand piece unit 4 includes a receptacle portion or stem 64 having a longitudinal axis A extending therethrough and a therapy distribution instrument 66. In the embodiment illustrated in FIGS. 4 and 5, the therapy distribution instrument 66 includes one or more probes 68 extending distally from the receptacle portion or stem 64 coaxial to axis A. The receptacle portion is also referred to as a stem because it resembles the stem of a plant. The receptacle portion or stem 64 acts as a handle and is configured and arranged to receive the therapy distribution instrument 66. The interior of the receptacle portion or stem 64 of the hand piece unit 4 is configured to house the components 32. The components 32, disposed in the receptacle portion or stem 64 and including the control unit 34, control the functions of the hand piece unit 4 to deliver therapy. The hand piece unit 4 may include a display connected to one or more of the components 32.

Figure 7:
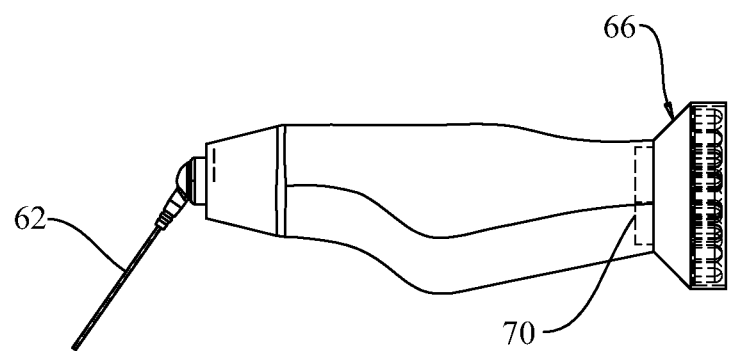
FIG. 7 is a side plan view of an embodiment of a hand piece unit of the facial muscle toner system wherein a cone shaped therapy distribution unit is attached to the hand piece unit.

The receptacle portion or stem 64 has one or more receiving connectors 70. In the embodiment shown in FIG. 4, the receiving connectors 70 are disposed coaxially to axis A on an external distal surface of the receptacle portion or stem 64. The receiving connectors 70 can also be disposed internally in the receptacle portion or stem 64, as shown in FIGS. 5-7. The receiving connectors 70 are preferably configured to receive a proximal end of the therapy distribution instrument 66. The therapy distribution instruments 66 have a mating connector 72 at the proximal end thereof. The mating connector 72 is configured for mating with the receiving connector 70. More preferably, the receiving connector 70 and the mating connector 72 have a plug-type mating configuration to provide secure, but releasable, frictional engagement of the receiving connector 70 with the mating connector 72. In other words, the receiving connector 70 and the mating connector 72 are female and male respectively. That is, the therapy distribution instrument 66 is releasably engaged with the receptacle portion or stem 64 such that the hand piece unit 4 has interchangeable therapy distribution instruments 66. Alternatively, the receiving connector 70 and the mating connector 72 may include inner and outer threads, respectively. An adapter (not shown) may be provided to adapt the particular receiving connector 70 to the mating connector 72 of the desired therapy distribution instrument 66. For example, an adapter may plug into the single receiving connector 70 of FIG. 6 to provide plural receiving connectors 70 as in FIG. 4 or 5.

In the embodiment wherein the therapy distribution instrument 66 includes one or more probes 68, the probes 68 have a therapy portion 74 at the distal end thereof. The therapy tip portion 74 includes a tip, roller, wires or LED to distribute a selected therapy to skin and/or sub-dermal muscles, as explained in more detail below. Embodiments of therapy distribution instruments 66 and the corresponding therapy tip portions 74 are illustrated in FIGS. 4-22. In view of the similarity between the embodiments, the parts of the embodiments that are identical will be given the same reference numerals. Thus, the descriptions of the identical parts of the embodiments may be omitted for the sake of brevity.

Figure 6A:
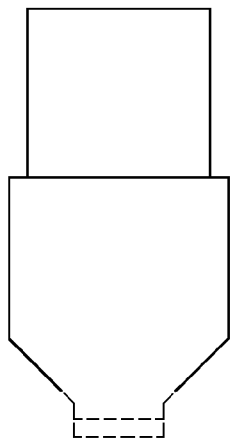
FIG. 6A is a side view of the thin metal blade and casing illustrated in FIG. 6.
Figure 6B:
FIG. 6B is a profile view of the thin metal blade and casing in FIG. 6A.
Figure 6C:
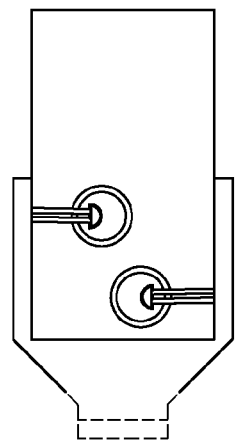
FIG. 6C is a side view of the thin metal blade with a portion of the casing removed to expose ultrasonic transducers on the thin metal blade.
Figure 7A:
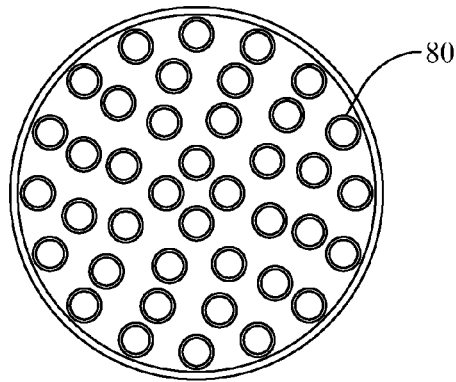
FIG. 7A is a top view of the cone shaped therapy distribution unit in FIG. 7 with LEDs.
Figure 7B:
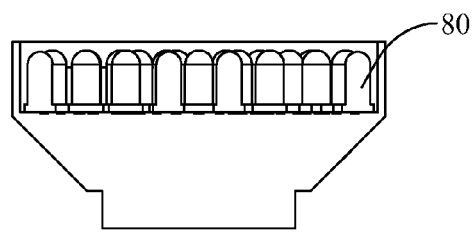
FIG. 7B is a partial cross sectional side view of the cone shaped therapy distribution instrument in FIGS. 7 and 7A.
Figure 7D:
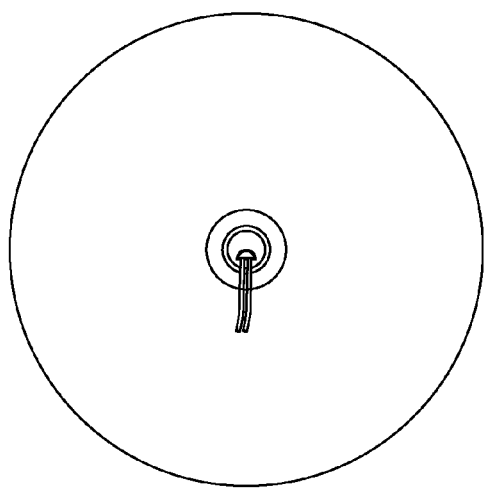
FIG. 7D is a bottom view of the ultrasonic applicator in FIG. 7C with the cone shaped casing removed to expose an ultrasonic transducer.
Figure 7C:
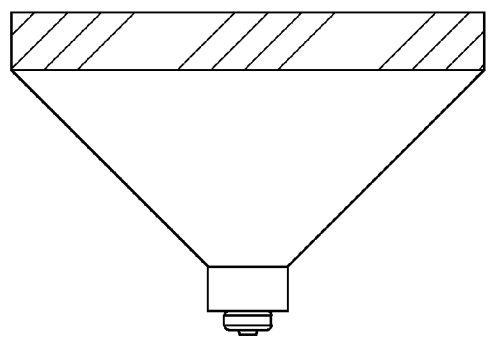
FIG. 7C is a side view of the cone shaped therapy distribution unit in FIG. 7 with an ultrasonic applicator.

An example of a therapy distribution instrument 66 that does not use probes for therapy is illustrated in FIGS. 6 and 7. Referring to FIGS. 6-6C, in this embodiment, the therapy distribution instrument 66 is a thin metal blade used for ultrasonic exfoliation. This ultrasonic therapy distribution instrument 66 is interchangeable with the receptacle portion or stem 64 and is removably attached to the receiving connectors 70. The therapy distribution instrument 66 includes a casing covering a bottom portion of the blade and housing ultrasonic transducers. Referring to FIG. 7, the therapy distribution instrument 66 has an approximate cone shape. As shown in FIGS. 7A and 7B, a bottom or distal end of the cone 66 houses a plurality of LEDs, which are configured and arranged to direct light therapy to the operator. FIGS. 7C and 7D illustrate an approximate cone shaped therapy distribution unit 66 with a closed bottom or distal end that houses an ultrasonic transducer. The therapy distribution instrument 66 of FIGS. 7C and 7D comprises an ultrasonic infuser used to infuse therapeutic solutions into the operator's skin.

Figure 9:
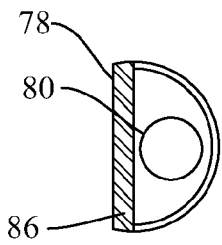
FIG. 9 is a top plan view of the embodiment of FIG. 8.
Figure 10:
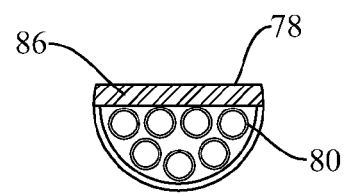
FIG. 10 is a top plan view of an alternative embodiment for an LED arrangement for the therapy tip portion of FIGS. 8 and 9.
Figure 8:
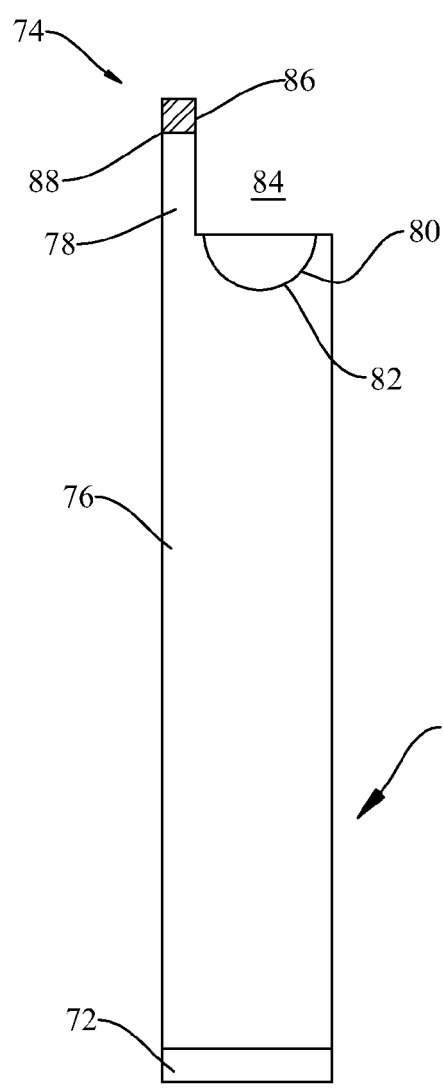
FIG. 8 is a side view of an embodiment of a therapy tip portion.
Figure 11:
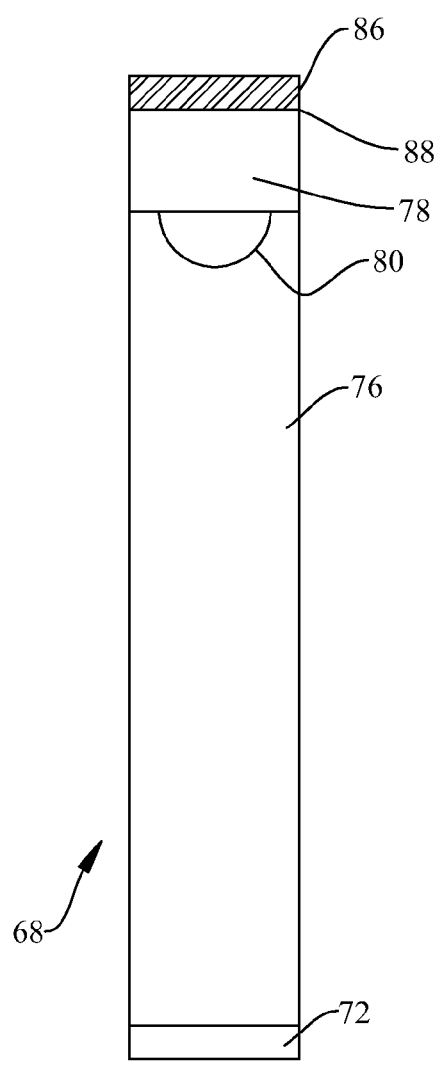
FIG. 11 is a front view of the embodiment of FIG. 8.

Referring to the embodiment shown in FIG. 8, the therapy portion 74 includes a main body portion 76 that connects with the mating connector 72 at a proximal end, an extended body 78 at a distal end and one or more LEDs 80 at the distal end. The main body portion 76 is a rigid member such that pressure can be applied to the face to manipulate the facial muscles. The main body portion 76 preferably comprises a plastic or metal alloy and has a semi-hemispherical cross-sectional shape. The main body portion 76 includes an LED holder 82 recessed within the main body portion 76 at the distal end. The LED holder 82 forms an opening for directing light distally. The LED holder 82 is sized and configured to hold one or more LEDs 80 as illustrated in FIGS. 9 and 10. The LEDs 80 provide light therapy to the operator and can be red, yellow, green, blue or infrared type LEDs, or combinations thereof.

The extended body 78 includes a rigid member that extends distally from the main body portion 76. The extended body 78 is of a smaller cross-section than the main body portion 76. Specifically, referring to FIGS. 9 and 10, the extended body 78 has a length substantially equal to a diameter of the main body portion 76. However, the thickness of the extended body 78 is reduced. The extended body 78 and the main body portion 76 form a light passage 84 therebetween. Specifically, the extended body 78 has a size that is smaller than the main body portion 76 and the light passage 84 is formed by the difference in size. A surface of the extended body 78 facing the light passage 84 can act as a partial light guide. The extended body 78 includes a metal tip 86 on a distal end portion 88 of the extended body 78. The metal tip 86 is connected to an electrical conduit (not shown), conducting a micro-current, disposed within the probe 68 and connected to power source 36. The metal tip 86 is sized, configured and arranged to deliver micro-current to skin tissue to provide a micro-current to skin tissue of the operator. The diameter of the body portion 76 may be expanded to provide more LEDs for more intensive light therapy.

Referring to FIG. 12, another embodiment of a therapy portion 74 includes a plastic or polymer tip 86 having a plurality of wires 90. The therapy portion 74 extends from the main body portion 76 and ends with a partially spherical head 92. The wires 90 wrap around the plastic portion and head 92 in a longitudinal direction. The wires 90 are exposed on the spherical head 92 and conduct micro-current to the skin. The wires 90 are connected to the power source 36, which generates the micro-current.

FIG. 13 illustrates another embodiment of the therapy portion 74. In this embodiment, wires 90 are wrapped about the head 92. The main body portion 76 has an LED 80 and an LED holder 82 for emitting light through the head 92. The LED 80 is disposed at an end of the main body portion 76 where the tip 86 connects to the main body portion 76. The plastic tip 86 is substantially transparent to allow light to shine through.

FIG. 14 illustrates another embodiment in which the therapy portion 74 of the embodiment in FIG. 13 is modified with one or more LEDs 80 in the plastic tip 86. The one or more LEDs 80 extend out of the main body portion 76 toward the head 92 to provide a more intense light therapy through the substantially transparent tip 86.

Figure 16:
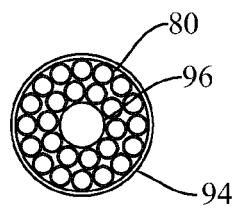
FIG. 16 is a top view of the embodiment of FIG. 15.
Figure 18:
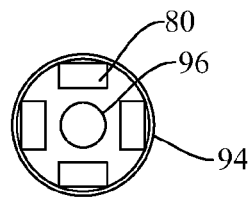
FIG. 18 is a top plan view of the embodiment of FIG. 17.
Figure 20:
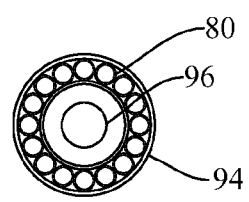
FIG. 20 is a top plan view of the embodiment of FIG. 19.
Figure 15:
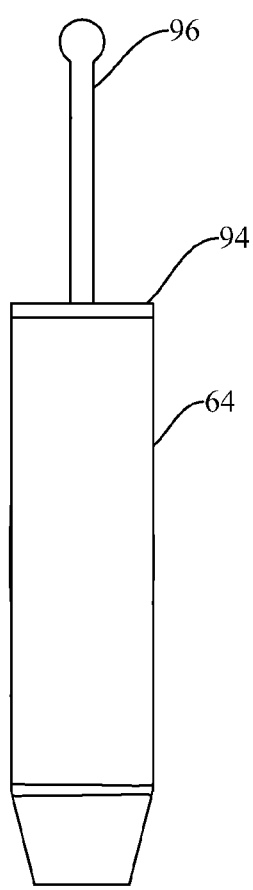
FIG. 15 is a side view of an embodiment of a therapy tip portion that delivers micro-current and light therapy.
Figure 17:
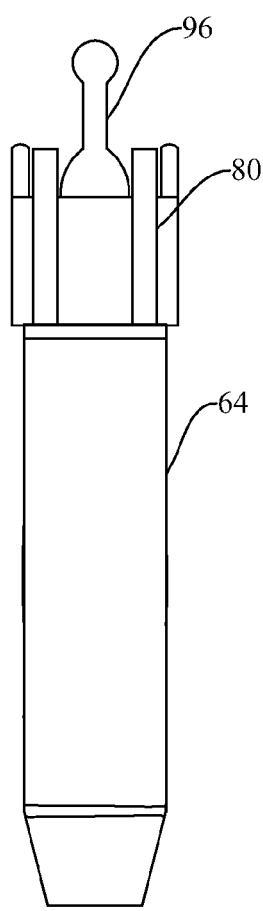
FIG. 17 is a side view of another embodiment of a therapy tip portion that delivers micro-current and light therapy.

Referring to FIGS. 15-20, various embodiments of a therapy portion 74 having a sleeve 94 and a metal applicator 96 extending distally are illustrated. The sleeve 94 holds and protects a plurality of LEDs 80 embedded therein, as shown in FIGS. 16, 18 and 20. The sleeve 94 and the metal applicator 96 are detachable from the receptacle portion 64. In FIGS. 15 and 16, the LEDs 80 are embedded in the sleeve 94 and surround a bottom portion of the metal applicator 96. In FIGS. 17 and 18, the LEDs 80 are on the side of the sleeve 94.

Figure 19:
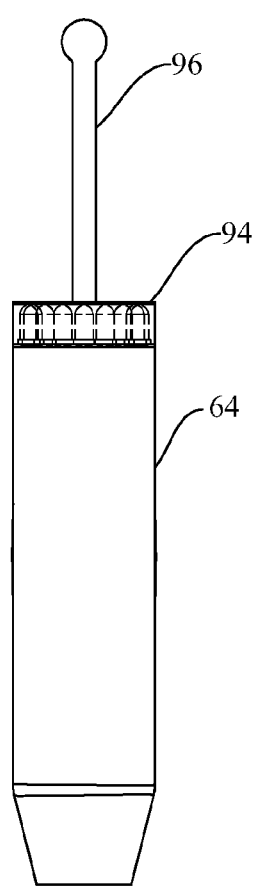
FIG. 19 is a side view of another embodiment of a therapy tip portion that delivers micro-current and light therapy.

Referring to FIGS. 19 and 20, a collar, formed by inner and outer sleeves 94, holds LEDs 80. While light therapy is delivered with LEDs, the metal applicator 96 can conduct micro-current for application to the skin. These embodiments are advantageous since both light therapy and micro-current therapy can be applied simultaneously.

Referring to FIGS. 21-27, an embodiment of the hand piece unit 4 having the receptacle portion or stem 64 and the therapy distribution instrument 66 includes two opposing conductive heads, which may be independently movable to grasp muscle or skin. The hand piece unit 4 of the present embodiment is designed for portability and use with one hand. The interior of the receptacle portion or stem 64 of the hand piece unit 4 is configured to house the components 32. The components 32, disposed in the receptacle portion or stem 64 and including the control unit 34, control the functions of the hand piece unit 4 to deliver therapy. The hand piece unit 4 may include a display connected to one or more of the components 32, as shown schematically in FIGS. 3A and 3B. Optionally, the hand piece unit 4 includes one or more buttons 120 to control the micro-current.

The receptacle portion or stem 64 includes a proximal end 63 and a distal end 65.

Figures 21, 22:
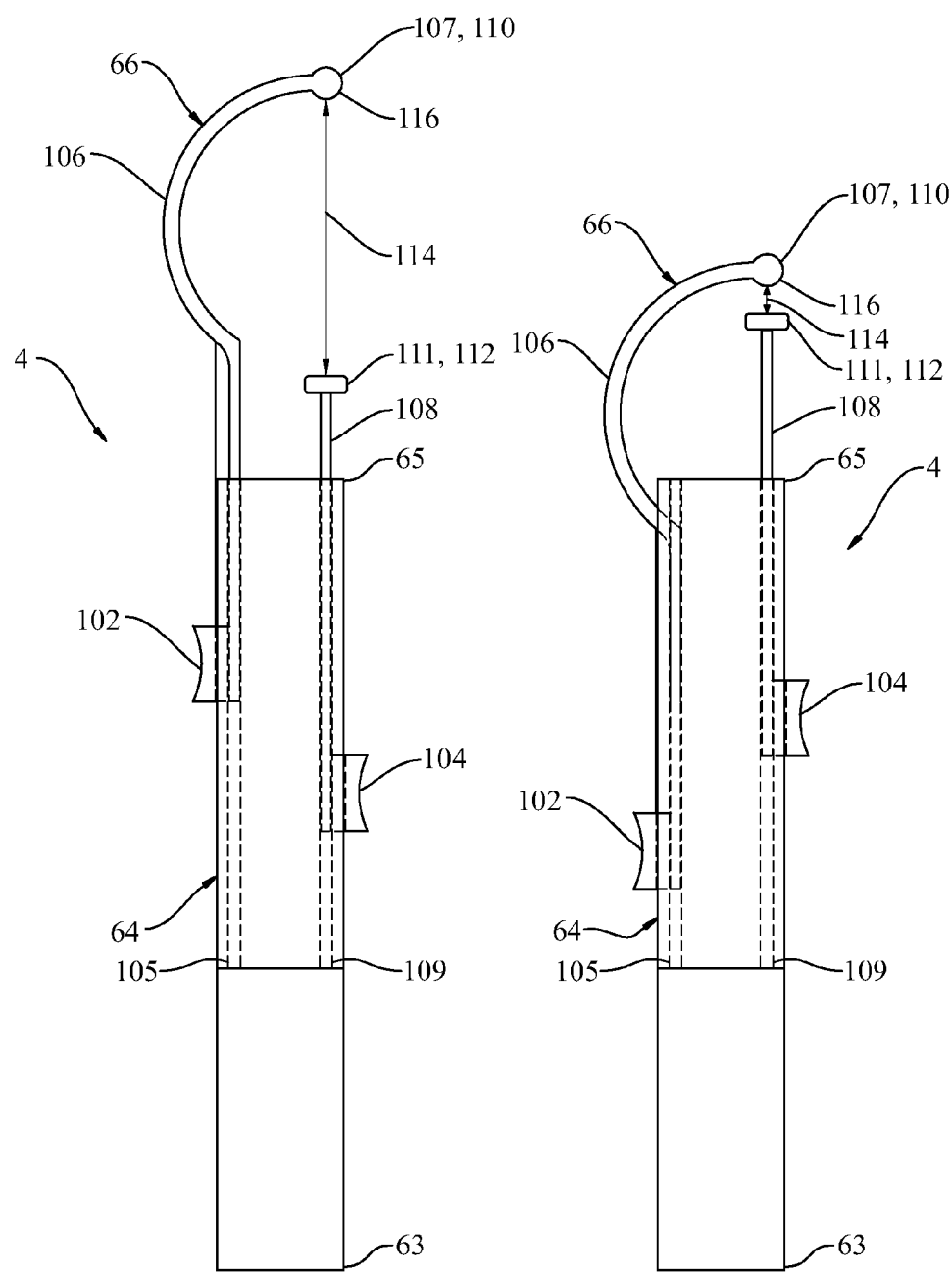
FIG. 21 is a side view of an embodiment of a receptacle and therapy distribution unit in an open position.
FIG. 22 is a side view of the embodiment of FIG. 21 in a closed position.
Figure 23:
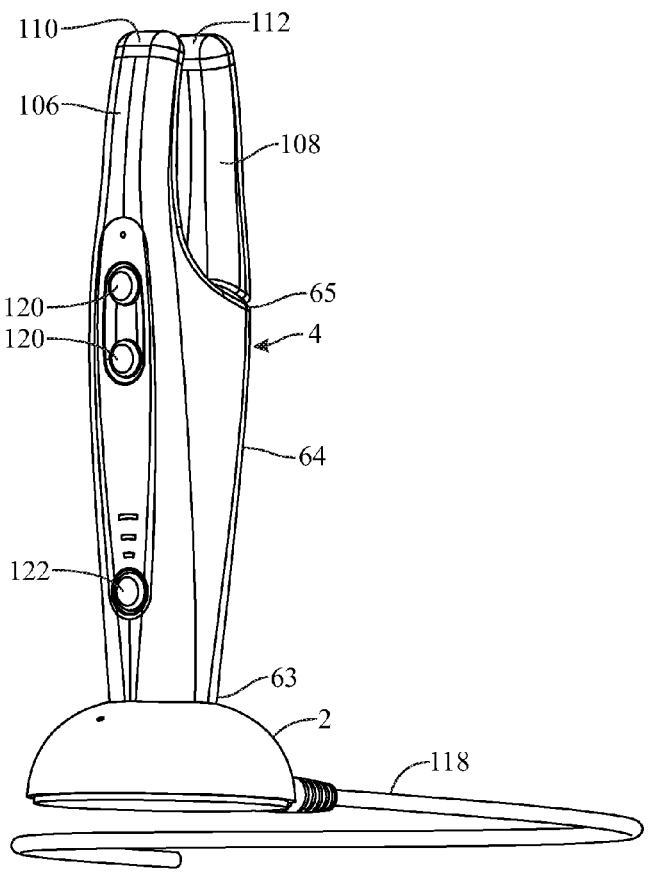
FIG. 23 is an isometric of an embodiment of a hand piece unit and a base unit.
Figure 24:
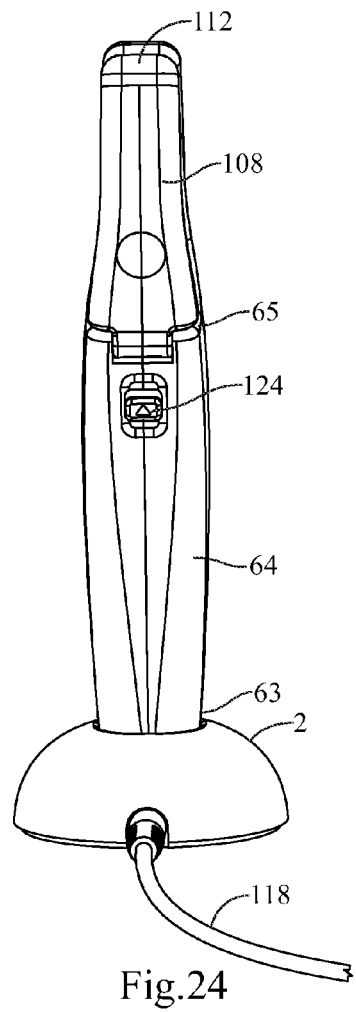
FIG. 24 is rear plan view of the embodiment of FIG. 23 with the hand piece unit attached to the base unit.
Figure 25:
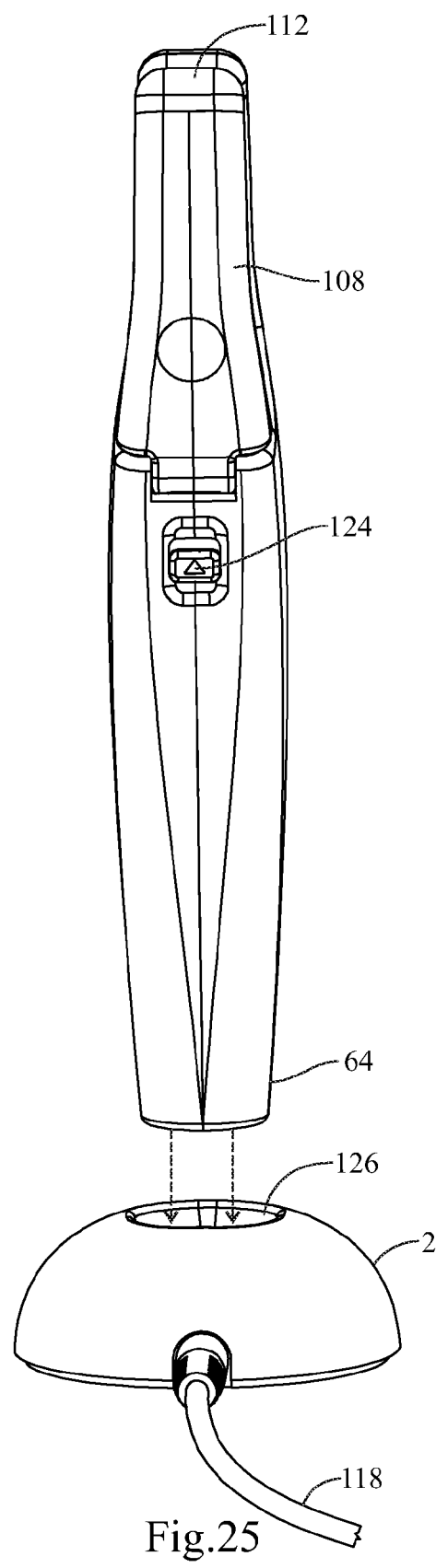
FIG. 25 is rear plan view of the embodiment of FIG. 23 with the hand piece unit not attached to the base unit.
Figure 26:
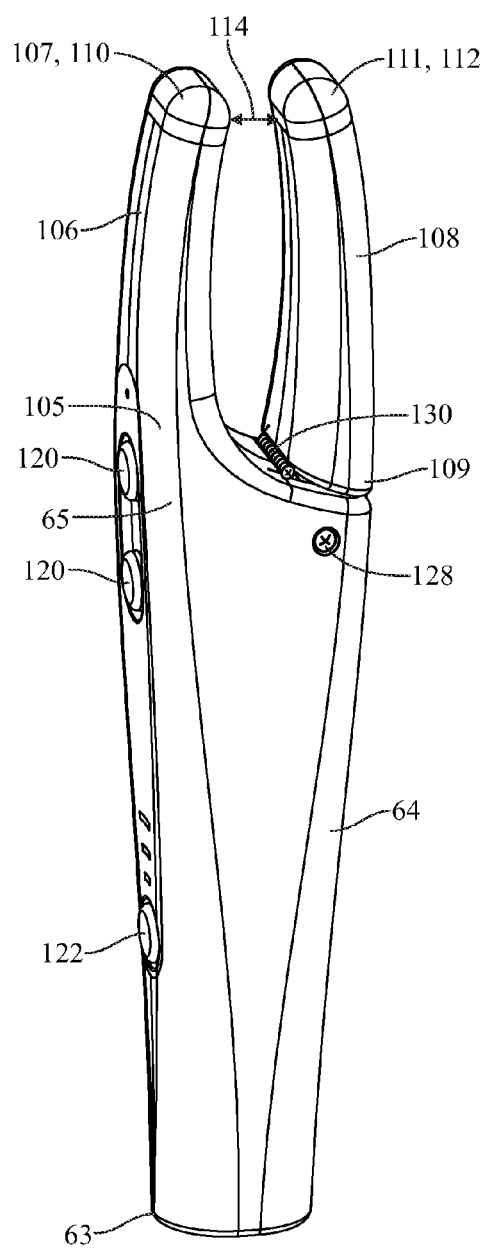
FIG. 26 is right plan view of the hand piece unit of FIG. 23.

In some embodiments, as shown in FIGS. 21-22, the receptacle portion or stem 64 includes a first actuator 102 and a second actuator 104, both of which are disposed on opposing sides of the receptacle portion or stem 64. The first and second actuators 102, 104 slide longitudinally along the exterior surface of the receptacle portion or stem 64. The therapy distribution instrument 66 includes a first rigid member 106 and a second rigid member 108. The first rigid member 106 is connected to the first actuator 102 and the second rigid member 108 is connected to the second actuator 104. It will be apparent to one of ordinary skill in the art from this disclosure that the first and second actuators 102, 104 can be actuated by an electric motor, for example, and can be disposed within the hand piece unit 4. The first and second rigid members 106, 108 extend upwardly/distally from the distal end 65 of the receptacle portion or stem 64. The first rigid member 106 has a proximal end 105, a distal end 107 and a substantially straight lower portion and a curvature at an upper/distal portion that curves across the width of the receptacle portion or stem 64 and towards the second rigid member 108.

The second rigid member 108 extends coaxially with axis A and is substantially straight and has a proximal end 109 and a distal end 111. The first rigid member 106 also has a first contact section 110 disposed at an end portion (e.g., the distal end 107) of the first rigid member 106. The second rigid member 108 includes a second contact section 112 disposed at an end portion (e.g., the distal end 111) of the second rigid member 108. The first and second contact sections 110, 112 are comprised of an exposed conductive material, such as copper, to deliver the micro-current therapy to the face. Conductors (not shown) run through the first and second rigid members 106, 108 to conduct the micro-current to the first and second contact sections 110, 112. Referring to FIG. 22, in operation, when the facial muscles are to be stretched, the first and second contact sections 110, 112 are adjacent each other and placed against the skin above a selected facial muscle. The first actuator 102 moves the first rigid member 106 and the first contact section 110 upwardly away from the second contact section 112 to form a treatment opening 114 so as to stretch out the facial muscle. The first and second actuators 102, 104 dictate the size of the treatment opening 114 by the direction of their movements. During the stretching and/or after, therapy is applied to the skin touching the first and second contact sections 110, 112 and the facial muscle underneath the area of skin. The therapy includes micro-current stimulation delivered through the skin to the facial muscle.

In another operation of the portable hand piece unit 4 of the present embodiment, the skin and facial muscles can be pinched or shortened. Specifically, the therapy distribution instrument 66 is placed on the skin over the selected facial muscle with the treatment opening 114 of sufficient magnitude to grasp the skin and facial muscle between the first and second contact sections, 110, 112. The first and second actuators 102, 104 then cause the first and second contact sections 110, 112 to pinch the skin and/or facial muscle while a micro-current stimulation is delivered.

In one embodiment, one or both of the first and second contact sections 110, 112 includes a roller 116. The roller 116 is rotatably disposed at the contact section 110, 112 and advantageously provides a rolling force on the muscle in a massaging action. The roller 116 is further advantageous when a rocking motion is desired during the micro-current stimulation.

Figure 27:
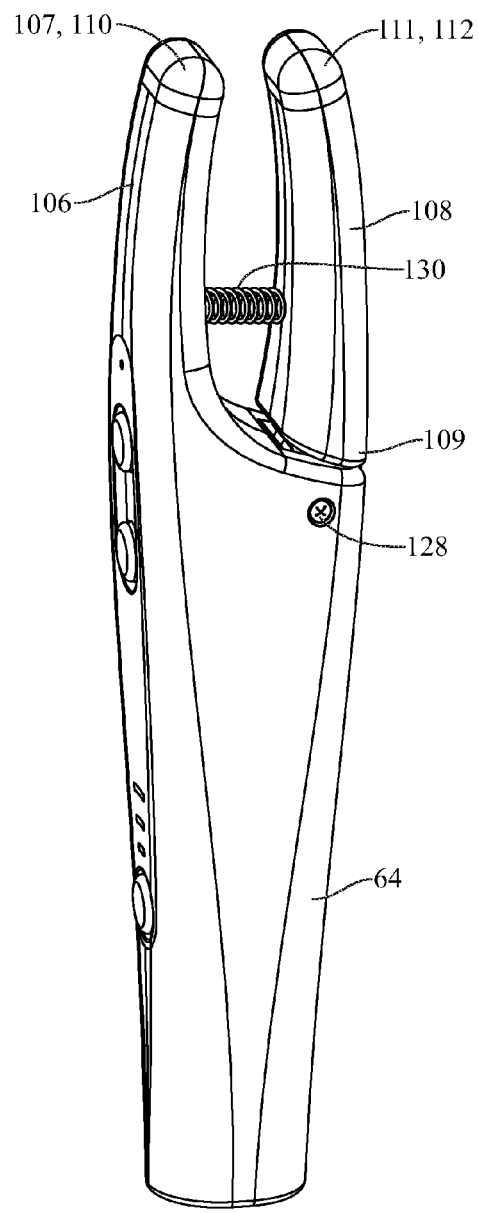
FIG. 27 is a left plan view of the hand piece unit of FIG. 23.

In another embodiment, as opposed to actuators 102 and 104, the system includes at least one pivot pin 128 and at least one spring 130 as shown in FIGS. 23-27, The pivot pin 128 is attached to the proximal end 105 or 109 of the first and/or second rigid member 106 or 108 and allows the first and/or second rigid member 106 or 108 to move (i.e., pivot) along an axis formed by the pivot pin 130 and toward the other rigid member 106 or 108. In some embodiments, the spring 130 is between the first and second rigid members 106 and 108, as shown in FIG. 27. Alternatively, the spring 130 may be located in the receptacle portion or stem 64 at the point of attachment of the first or second rigid member 108 to the receptacle portion or stem 64. In some embodiments, the pivot bolt 128 passes through the spring 130. Optionally, the receptacle portion or stem 64 contains a battery 36 that is charged by placing the proximal end 63 of the receptacle portion or stem 64 in a recess 126 in the base portion 2 and the base portion 2 is coupled to an external power source (e.g., a wall plug) by a wire 118. Preferably the entire system is portable. The system may further include conductors (not shown) which run through the first and second rigid members 106, 108 to conduct the micro-current to the first and second contact sections 110, 112. Optionally, the receptacle portion or stem 64 further includes at least one button 120 configured to control the micro-current, an on/off switch 122 and a display 20. Optionally, the receptacle portion or stem 64 further includes a control unit 34 that includes a microcomputer 38 configured to control the system and the microcomputer 38 includes a memory storage device. Optionally, the receptacle portion or stem 64 further includes a lock 124 configured to lock the position of the second rigid member 108 relative to the first rigid member 106. Optionally, the hand piece unit 4 is provided as a two piece design with the receptacle portion or stem 64 and first rigid member 106 being one piece and the second rigid member being a second piece, as illustrated in FIGS. 23-27.

Optionally, the system of FIGS. 21-27 is used in a method of introducing a micro-current to the face of a human that includes:
a) providing the system;
b) placing the first and second contact sections 110 and 112 on the human's face; and
c) delivering a micro-current to the first and second contact sections 110 and 112.

Optionally, the method further includes pinching the human's face using the first and second contact sections 110 and 112. Optionally, the method further includes using the micro-current to stretch muscles of the human's face. Optionally, the method further includes using the micro-current to re-educate muscles of the human's face.

In understanding the scope of the present invention, the term "configured" as used herein to describe a component, section or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, and/or steps, but do not exclude the presence of other unstated features, elements, components, groups, and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:
1. A facial muscle toner system comprising:
a treatment applicator having an expanded state and a collapsed state, the treatment applicator in the shape of a fork in the expanded state and comprising:
a stem having a proximal end, a distal end, and a length extending from the proximal end to the distal end of the stem;
a first rigid arm forking from the distal end of the stem, the first rigid arm having a proximal end and a distal end, the first rigid arm comprising an exposed conductive material, the first rigid arm fixed relative to the stem;
a second rigid arm forking from the distal end of the stem, the second rigid arm having a proximal end and a distal end, the second rigid arm comprising an exposed conductive material, the second rigid arm pivotally attached to the stem by a pivot pin, the pivot pin creating a pivot axis, the second rigid arm configured to pivot along the pivot axis toward the first rigid arm;
a cavity comprising a bottom defined by the distal end of the stem, a first side defined by the first rigid arm, and a second side defined by the second rigid arm;
a power source configured to deliver a micro-current to the exposed conductive material of the first and second rigid arms; and
a spring attached to the stem and the second rigid arm;
wherein the pivot pin is located adjacent to the bottom of the cavity and further wherein the pivot pin is located adjacent to the proximal end of the second rigid arm and further wherein the spring is located adjacent to the pivot pin.

2. The system of claim 1, wherein the power source is a battery.

3. The system of claim 1, wherein the stem comprises a stem interior, further wherein the power source is a battery and further wherein the battery is located in the stem interior.

4. The system of claim 1, wherein the stem comprises an interior and the stem interior comprises the power source and a control unit comprising a microcomputer configured to control the system and further wherein the microcomputer comprises a memory storage device.

5. The system of claim 1, wherein the distal ends of the first and second rigid arms are curved towards each other in the expanded state.

6. The system of claim 5, wherein the first and second rigid arms are generally in the shape of an arc in the expanded state.

7. The system of claim 1, wherein the stem further comprises a button configured to control the micro-current and a display.

8. The system of claim 1, wherein the system further comprises a base unit, the base unit having a recess configured to receive the proximal end of the stem.

9. The system of claim 8, wherein the base unit is coupled to a power source by a wire.

10. The system of claim 1 wherein the stem is generally straight.

11. The system of claim 1 wherein the stem and the first rigid arm are a single unit.

12. The system of claim 1 wherein the pivot pin comprises a slotted head.

13. A method of introducing a micro-current to the face of a human, the method comprising the steps of:
   a) providing the system of claim 1;
   b) placing the exposed conductive material of the first and second rigid arms on the human's face; and
   c) delivering a micro-current to the exposed conductive material of the first and second rigid arms.

14. The method of claim 13, wherein the method further comprises pinching the human's face using the exposed conductive material of the first and second rigid arms.

15. The method of claim 13, wherein the method further comprises using the micro-current to stretch muscles of the human's face.

16. The method of claim 13, wherein the method further comprises using the micro-current to re-educate muscles of the human's face.

17. The method of claim 13, wherein the stem further comprises a button configured to control the micro-current and the method further comprises using the button to control the micro-current.

\* \* \* \* \*